United States Patent
Okabayashi et al.

(10) Patent No.: US 6,685,636 B2
(45) Date of Patent: Feb. 3, 2004

(54) ULTRASONIC TOMOGRAPHY APPARATUS AND ULTRASONIC TOMOGRAPHY METHOD

(75) Inventors: Ichiro Okabayashi, Ikoma (JP); Manabu Migita, Neyagawa (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/191,226

(22) Filed: Jul. 9, 2002

(65) Prior Publication Data

US 2003/0023165 A1 Jan. 30, 2003

(30) Foreign Application Priority Data

Jul. 9, 2001 (JP) .................................. 2001-208488

(51) Int. Cl.[7] ................................................. A61B 8/00
(52) U.S. Cl. ...................................... 600/437; 600/453
(58) Field of Search ................................. 600/437, 438, 600/440–447, 449–459, 460–471; 73/625, 626; 367/7, 11, 130, 138; 128/916

(56) References Cited

U.S. PATENT DOCUMENTS

| | | | |
|---|---|---|---|
| 4,622,977 A | | 11/1986 | Namekawa et al. |
| 5,501,224 A | * | 3/1996 | Shiki ........................... 600/456 |
| 5,628,322 A | * | 5/1997 | Mine ........................... 600/453 |
| 5,924,991 A | * | 7/1999 | Hossack et al. ............ 600/443 |
| 6,023,977 A | * | 2/2000 | Langdon et al. ............... 73/629 |
| 6,132,374 A | * | 10/2000 | Hossack et al. ............ 600/443 |
| 6,419,632 B1 | * | 7/2002 | Shiki et al. ................. 600/443 |

OTHER PUBLICATIONS

GE Medical Systems, Ultrasound Technical Tutorials, B–Flow, http://www.gemedicalsystems.com/rad/us/education/msutut4.html.

"Basic Ultrasonic Medicine" (Ishiyaku Publishing Inc.), pp. 55–57.

* cited by examiner

Primary Examiner—Ali M. Imam
(74) Attorney, Agent, or Firm—RatnerPrestia

(57) ABSTRACT

An ultrasonic tomography apparatus has an ultrasonic transmitter for transmitting an ultrasound to an object body; an ultrasonic receiver for receiving ultrasound reflected from an object body and producing an ultrasonic signal; a filter for extracting components of the ultrasonic signal in at least two different frequency bands; and an image generator for generating an ultrasonic tomogram of the object body based on the extracted ultrasonic signal component in a first frequency band and the extracted ultrasonic signal component in one or more second frequency bands. The first frequency band centers on a frequency band at the time of transmission, and the second frequency band is shifted from the frequency band at the time of transmission.

19 Claims, 16 Drawing Sheets

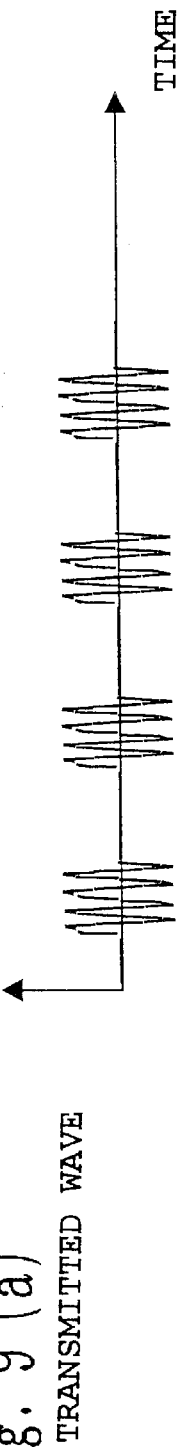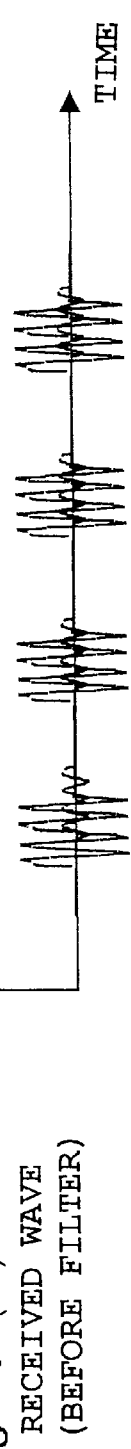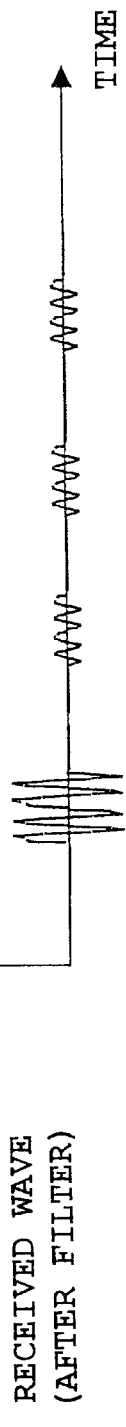
Fig. 9(a) TRANSMITTED WAVE
Fig. 9(b) RECEIVED WAVE (BEFORE FILTER)
Fig. 9(c) RECEIVED WAVE (AFTER FILTER)

ULTRASONIC TOMOGRAPHY APPARATUS AND ULTRASONIC TOMOGRAPHY METHOD

BACKGROUND OF THE INVENTION

1. Field of the Invention

The present invention relates to an image display apparatus or the like that displays a blood flow in an ultrasonic diagnostic apparatus, and more particularly, to an image display apparatus involving a B-mode method (tomogram display).

2. Description of the Related Art

The ultrasonic diagnostic apparatus is to display a tomogram based on an ultrasonic signal reflected from an object body, and a method of displaying the tomogram in real time is referred to as a B-mode method.

The B-mode method has a disadvantage in that, while it allows tissues of the object body to be displayed with good quality, when displaying a blood flow in a blood vessel, the image thereof becomes blurred. To overcome the disadvantage, an attempt involving a digital technology has been made as follows. FIG. 10 illustrates an operation of a method of displaying a blood flow in the conventional ultrasonic diagnostic apparatus. This is referred to as a B-Flow, which is disclosed in the web site of http://www.gemedicalsystems.com/rad/us/education/msutut4.html.

With reference to FIG. 10, the operation of the conventional ultrasonic diagnostic apparatus will be described below. First, an encoder 20 emits an ultrasonic beam. The ultrasound reflected from a human body 2 (referred to as an echo, hereinafter) is decoded in a decoder 21, and then displayed in B-mode.

Here, as shown in FIG. 16, a blood flow 161 lies deeper in the object body than a tissue 160. Thus, for an incident ultrasonic beam 162, a blood flow echo 163b and a tissue echo 163a return with a time lag, so that the two echoes can be distinguished. Since the blood flow echo is weaker than the tissue echo, the sensitivity is enhanced when receiving the blood flow echo. The time lag between the reflection echoes is due to a fact that the tissue echo is contributed by a reflection from a blood vessel wall and the blood flow echo is primarily contributed by a scattering from a red blood cell in the blood vessel. The encoder 20 and the decoder 21 are used to distinguish and superimpose the weak reflection echoes. That is, according to an encoded pattern, signals received at the timing of "1" are added, and the result is regarded as the received echo. Strictly speaking, the reflection echo due to the thickness of the tissue 160 includes echoes from a tissue surface and from an interface with the blood flow. For simplicity, however, only the latter is shown in FIG. 16.

According to the above arrangement, however, the blood flow echo and the tissue echo are distinguished based on the time lag therebetween, and thus, cannot be separated if they are close to each other. That is, it is difficult to display the blood flow near the blood vessel wall or the blood flow in a thin blood vessel. In addition, since the blood flow echo and the tissue echo are close to each other, it is difficult to adjust the amplification factor thereof. For example, if the amplification factor is enhanced to be adapted for the blood flow, there is a possibility that the whole image becomes too bright, and a whitish image is provided.

In short, with the conventional ultrasonic tomography, when a tomogram for the whole object body is generated in B-mode, a vivid image of the blood flow cannot be produced.

There is another approach of utilizing the Doppler effect to derive from the received ultrasonic signal a phase difference between a wave reflected from the blood flow and a wave reflected from the tissue, calculating velocity data of a section of the blood flow, that is, direction and intensity data thereof based on the phase difference, generating a color image reflecting the velocity of the flow, and superimposing the color image on the B-mode image for display. This approach is referred to as Color Flow, and is disclosed in "Basic Ultrasonic Medicine" (Ishiyaku Publishing Inc.), p. 55–57 and U.S. Pat. No. 4,622,977, for example. The entire disclosure of the each publication is incorporated herein by reference in its entirety.

However, the Color Flow requires dedicated image processing means that involves an enormous amount of complicated calculation such as an autocorrelation operation or fast Fourier transform, and thus, the whole apparatus is complicated and the cost is increased. Furthermore, the Color Flow cannot provide an actual image of the blood flow, so that the image provided is poor in reality.

In view of the problems described above, this invention aims to provide an ultrasonic tomography apparatus and an ultrasonic tomography method that can, with a simple and inexpensive arrangement, display an image of a tissue and blood flow in an object body in B-mode such vividly that they can be easily distinguished.

SUMMARY OF THE INVENTION

One aspect of the present invention is an ultrasonic tomography apparatus, comprising:

ultrasonic transmitting means of transmitting an ultrasound to an object body;

ultrasonic receiving means of receiving the ultrasound reflected from said object body and producing an ultrasonic signal;

filtering means of extracting components of said ultrasonic signal in at least two different frequency bands; and image generating means of generating an ultrasonic tomogram of said object body based on said extracted ultrasonic signal component in a first frequency band and said extracted ultrasonic signal component in one or more second frequency bands, wherein said first frequency band centers on a frequency band at the time of said transmission, and said second frequency band is shifted from the frequency band at the time of said transmission.

Another aspect of the present invention is an ultrasonic tomography apparatus, comprising:

ultrasonic transmitting means of transmitting an ultrasound to an object body;

ultrasonic receiving means of receiving the ultrasound reflected from said object body and producing an ultrasonic signal;

filtering means of extracting components of said ultrasonic signal in at least two different frequency bands; and image generating means of generating a first partial ultrasonic tomogram of said object body based on said extracted ultrasonic signal component in a first frequency band and a second partial ultrasonic tomogram of said object body based on said ultrasonic signal component in one or more second frequency bands, wherein said first frequency band centers on a frequency band at the time of said transmission, and said second frequency band is shifted from the frequency band at the time of said transmission.

Still another aspect of the present invention is the ultrasonic tomography apparatus further comprising:

image processing means of performing an image processing on at least one of said first partial ultrasonic tomogram and said second partial ultrasonic tomogram; and image synthesizing means of producing an ultrasonic tomogram by performing any of (1) synthesis of the first partial ultrasonic tomogram subject to said image processing and the second partial ultrasonic tomogram not subject to said image processing, (2) synthesis of the first partial ultrasonic tomogram not subject to said image processing and the second partial ultrasonic tomogram subject to said image processing, and (3) synthesis of the first partial ultrasonic tomogram subject to said image processing and the second partial ultrasonic tomogram subject to said image processing.

Yet still another aspect of the present invention is the ultrasonic tomography apparatus, wherein said second frequency band is set centering on a frequency for which a signal component having a level more than predetermined one is detected by scanning a predetermined bandwidth allowing for a potential Doppler shift from said first frequency band.

Still yet another aspect of the present invention is the ultrasonic tomography apparatus, wherein said second frequency band is set centering on a frequency for which a signal component having a level more than predetermined one is detected by frequency-analyzing said received reflected ultrasonic.

A further aspect of the present invention is the ultrasonic tomography apparatus, wherein said filtering means includes:

a first sub-filter for allowing said first frequency band to pass therethrough; and one or more second sub-filters for allowing said second frequency band to pass therethrough.

A still further aspect of the present invention is the ultrasonic tomography apparatus, wherein said filtering means is set a first pass band for allowing said first frequency band to pass through the filtering means and a second pass band for allowing said second frequency band to pass through the filtering means, and said first pass band and said second pass band allow signals to pass therethrough simultaneously.

A yet further aspect of the present invention is the ultrasonic tomography apparatus, wherein said filtering means allows said first frequency band or said second frequency band to pass therethrough selectively, and said image generating means performs an operation using the ultrasonic signal component in said first frequency band and an operation using the ultrasonic signal component in said second frequency band in a time-divisional manner.

Still yet further aspect of the present invention is the ultrasonic tomography apparatus, wherein in said filtering means, the number of times of selection of said second frequency band is higher than that of said first frequency band.

An additional aspect of the present invention is the ultrasonic tomography apparatus, wherein said image generating means includes amplifying means of amplifying a signal having passed through said first frequency band and/or a signal having passed through said second frequency band, and said amplifying means amplifies the signal having passed through said second frequency band more than the signal having passed through said first frequency band.

A still additional aspect of the present invention is the ultrasonic tomography apparatus, wherein said object body is a human body, said first frequency band is a frequency band of an echo from a tissue of said human body, and said second frequency band is a frequency band of an echo from a blood flow in said human body.

A yet additional aspect of the present invention is the ultrasonic tomography apparatus, wherein said filtering means includes:

a first sub-filter for allowing said first frequency band to pass therethrough; and one or more second sub-filters for allowing said second frequency band to pass therethrough.

A still yet additional aspect of the present invention is the ultrasonic tomography apparatus, wherein said filtering means is set a first pass band for allowing said first frequency band to pass through the filtering means and a second pass band for allowing said second frequency band to pass through the filtering means, and said first pass band and said second pass band allow signals to pass therethrough simultaneously.

A supplementary aspect of the present invention is the ultrasonic tomography apparatus, wherein said filtering means allows said first frequency band or said second frequency band to pass therethrough selectively, and said image generating means performs an operation using the ultrasonic signal component in said first frequency band and an operation using the ultrasonic signal component in said second frequency band in a time-divisional manner.

A still supplementary aspect of the present invention is the ultrasonic tomography apparatus, wherein in said filtering means, the number of times of selection of said second frequency band is higher than that of said first frequency band.

A yet supplementary aspect of the present invention is the ultrasonic tomography apparatus, wherein said image generating means includes amplifying means of amplifying a signal having passed through said first frequency band and/or a signal having passed through said second frequency band, and said amplifying means amplifies the signal having passed through said second frequency band more than the signal having passed through said first frequency band.

A still yet supplementary aspect of the present invention is the ultrasonic tomography apparatus, wherein said object body is a human body, said first frequency band is a frequency band of an echo from a tissue of said human body, and said second frequency band is a frequency band of an echo from a blood flow in said human body.

Another aspect of the present invention is an ultrasonic tomography method, comprising the steps of:

transmitting an ultrasound to an object body;

receiving the ultrasound reflected from said object body;

extracting components of said ultrasound in at least two different frequency bands; and generating an ultrasonic tomogram of said object body based on said extracted ultrasonic component in a first frequency band and said extracted ultrasonic component in one or more second frequency bands, wherein said first frequency band centers on a frequency band at the time of said transmission, and said second frequency band is shifted from the frequency band at the time of said transmission.

Still another aspect of the present invention is an ultrasonic tomography method, comprising the steps of:

transmitting an ultrasound to an object body;

receiving the ultrasound reflected from said object body;

extracting components of said ultrasonic in at least two different frequency bands;

generating a first partial ultrasonic tomogram of said object body based on said extracted ultrasonic signal component in a first frequency band; and generating a second partial ultrasonic tomogram of said object body based on said extracted ultrasonic signal component in one or more second frequency bands, wherein said first frequency band centers on a frequency band at the time of said transmission, and said second frequency band is shifted from the frequency band at the time of said transmission.

Yet still another aspect of the present invention is the ultrasonic tomography method, wherein said second frequency band is set centering on a frequency for which a signal component having a level more than predetermined one is detected by scanning a predetermined bandwidth allowing for a potential Doppler shift from said first frequency band.

Still yet another aspect of the present invention is the ultrasonic tomography method, wherein said second frequency band is set centering on a frequency for which a signal component having a level more than predetermined level is detected by frequency-analyzing said received reflected ultrasonic.

BRIEF DESCRIPTION OF THE DRAWINGS

FIG. 9A is a timing chart (on a transmitter side) of switching filter characteristics of the band pass filtering means 3d of the embodiment 3 of this invention;

FIG. 9B is a timing chart (on a receiver side) of switching filter characteristics of the band pass filtering means 3d of the embodiment 3 of this invention;

FIG. 9C is a timing chart (after filtering) of switching filter characteristics of the band pass filtering means 3d of the embodiment 3 of this invention;

DESCRIPTION OF SYMBOLS

1 TRANSMITTING MEANS
2 HUMAN BODY
3a, 3b BAND PASS FILTERING MEANS
4 B-MODE DISPLAY SCREEN
5 BLOOD FLOW
6 BLOOD VESSEL WALL
10 TRANSMITTING/RECEIVING UNIT
11 AD CONVERTING UNIT
12 BAND PASS FILTERING (BPF) UNIT
13 DETECTING UNIT
14 AMPLIFING UNIT
15 LOW-PASS FILTERING (LPF) UNIT
16 IMAGE GENERATING UNIT
17 FRAME MEMORY (FM) UNIT
18 DISPLAYING UNIT
20 ENCODER
21 DECODER

DETAILED DESCRIPTION OF THE PREFERRED EMBODIMENTS

Now, embodiments of this invention will be described with reference to the drawings below.

(Embodiment 1)

Figure 1:
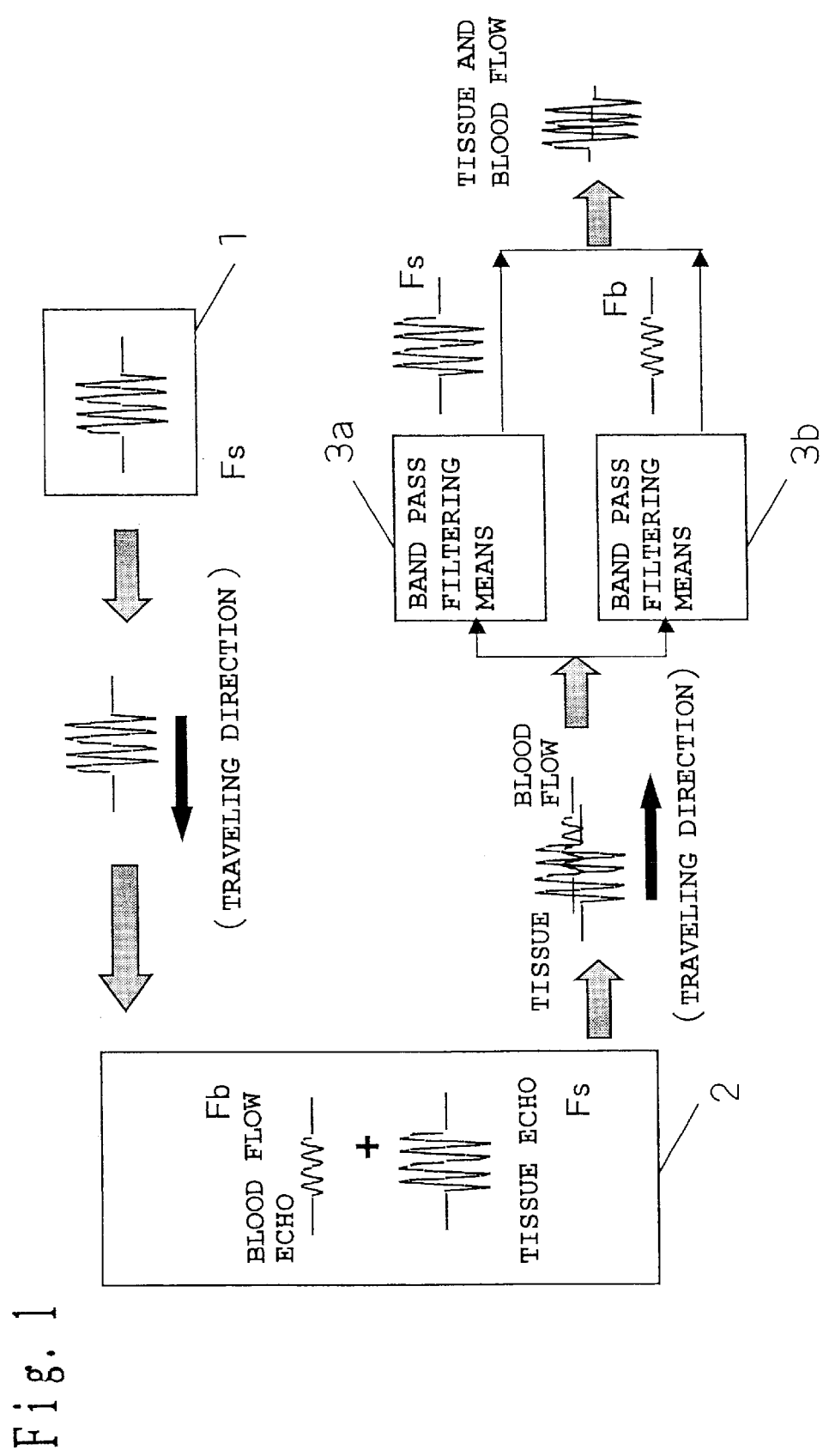
FIG. 1 is a diagram illustrating an operation of a method of imaging a blood flow according to an embodiment 1 of this invention.
Figure 2:
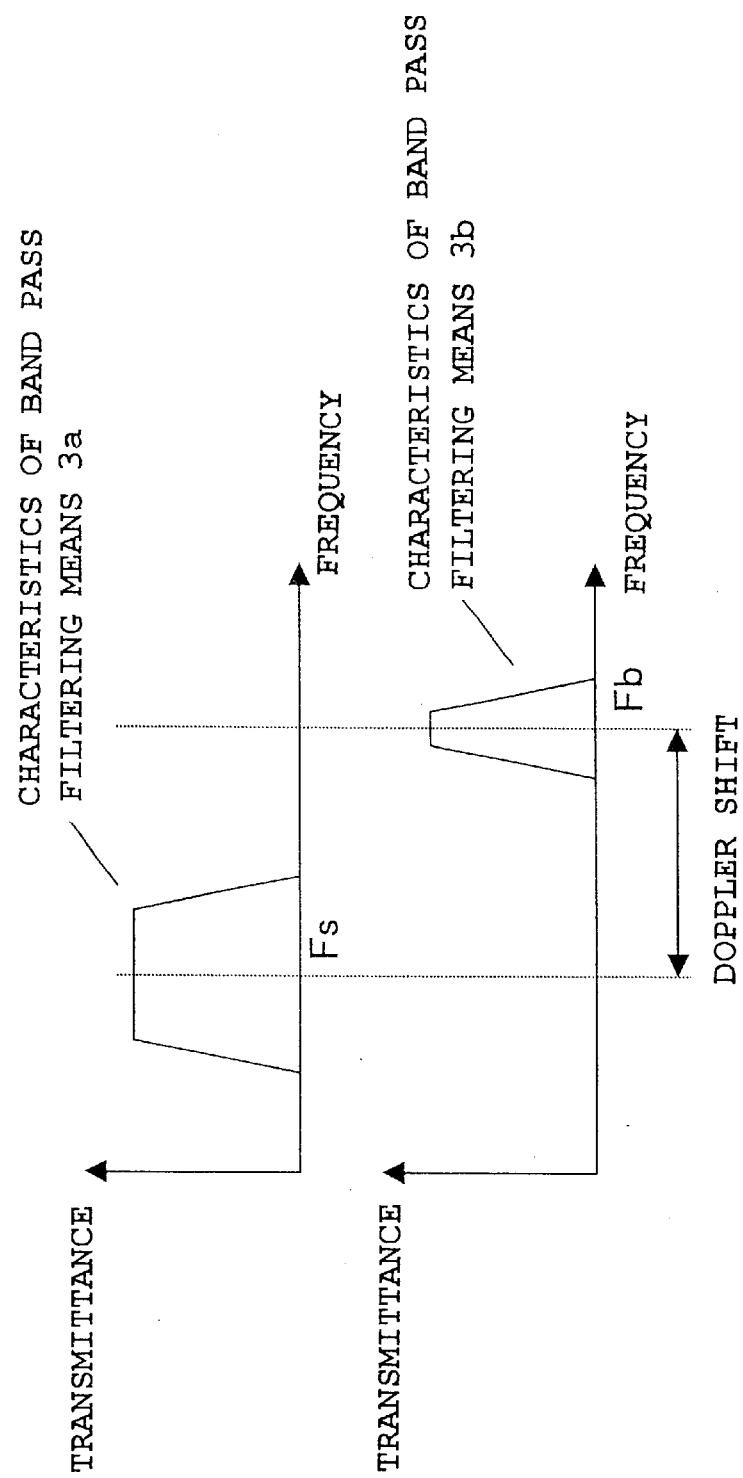
FIG. 2 shows characteristics of band pass filtering means in the embodiment 1 of this invention.
Figure 3:
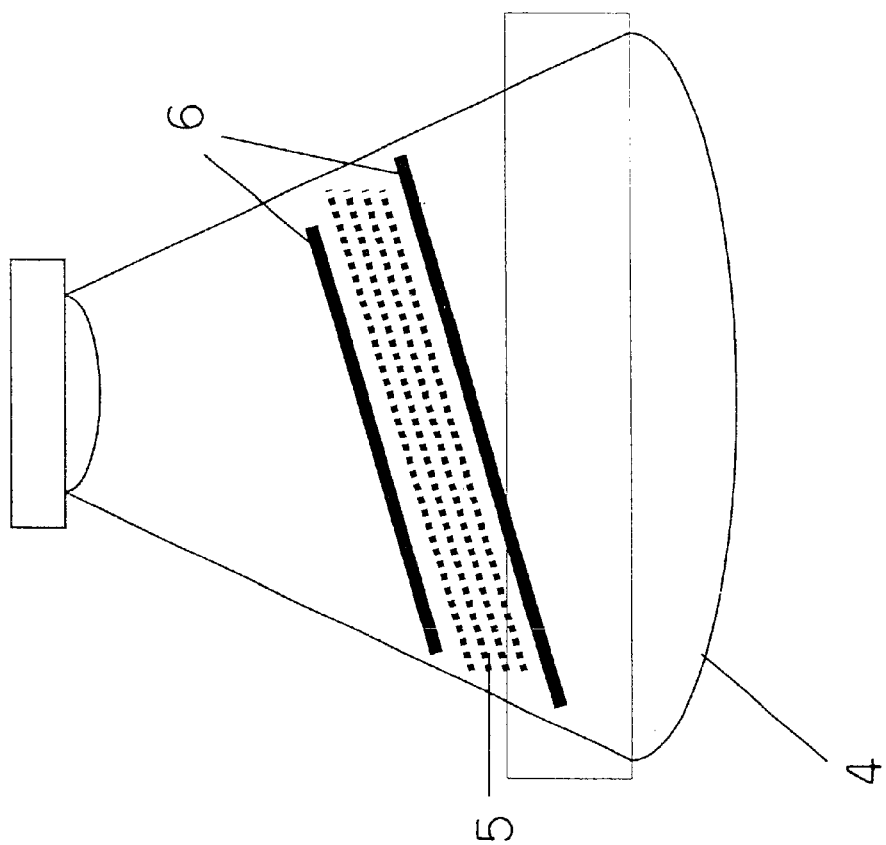
FIG. 3 shows a B-mode image (tomogram display) displayed in the embodiment 1 of this invention.
Figure 4:
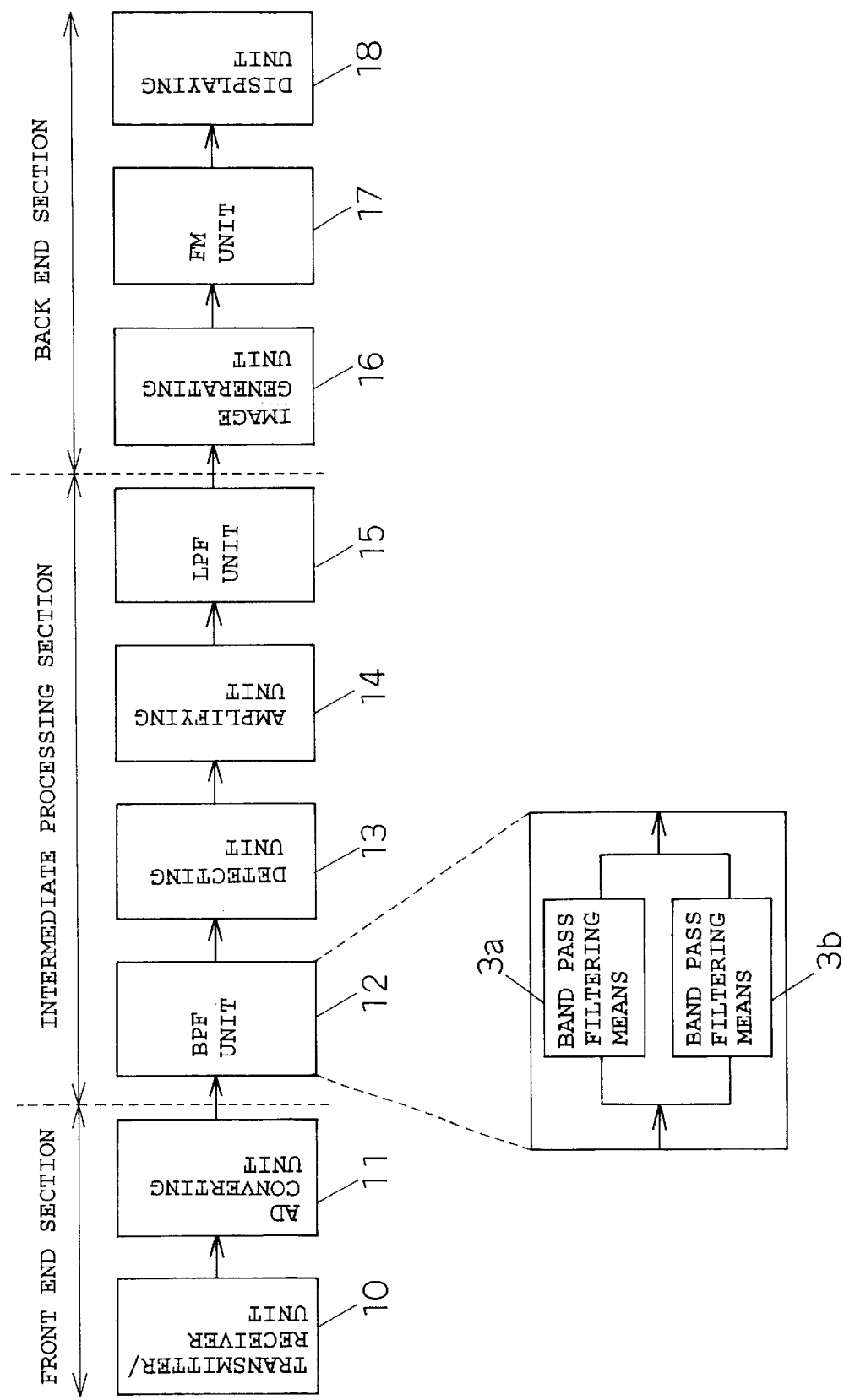
FIG. 4 is a block diagram showing an ultrasonic diagnostic apparatus that implements the method of imaging a blood flow according to the embodiment 1 of this invention.

A method of imaging a blood flow according to an embodiment 1 of this invention will be described with reference to the drawings below. FIG. 1 is a schematic diagram for illustrating an operation of the method of imaging a blood flow according to an embodiment 1 of this invention. FIG. 2 shows characteristics of band pass filter means in the embodiment. FIG. 3 shows a B-mode image (tomogram display) displayed in the embodiment. FIG. 4 is a block diagram showing an ultrasonic diagnostic apparatus that implements the imaging method.

In these drawings, reference numeral 1 denotes a transmitting means, reference numeral 2 denotes a human body, reference numerals 3a, 3b denote band pass filter means, reference numeral 4 denotes a B-mode display screen, reference numeral 5 denotes a blood flow, and reference numeral 6 denotes a blood vessel wall. In addition, reference numeral 10 denotes a transmitting/receiving unit that transmits or receives ultrasound, reference numeral 11 denotes an AD converting unit, reference numeral 12 denotes a band pass filtering (BPF) unit, reference numeral 13 denotes a detecting unit, reference numeral 14 denotes an amplifying unit, reference numeral 15 denotes a low-pass filtering (LPF) unit, reference numeral 16 denotes an image generating unit, reference numeral 17 denotes a frame memory (FM) unit that stores the image generated in the image generating unit 16 by the frame, and reference numeral 18 denotes a displaying unit.

Referring to FIG. 1, the method of imaging a blood flow according to this embodiment will be described. First, the transmitting means 1 emits a ultrasonic beam having a center frequency Fs. The ultrasonic beam is reflected from a part in the human body 2 at which an acoustic impedance is changed. Since tissues of internal organs, blood vessels, bones and the like in the human body 2 are stationary objects, the reflected wave therefrom (referred to as a tissue echo) has the center frequency Fs unchanged.

On the contrary, the blood flow is moving in the blood vessel in the human body 2. Thus, the reflected wave therefrom (referred to as a blood flow echo) is Doppler-shifted and has a center frequency Fb different from the center frequency Fs of the transmitted wave. The reflection is primarily contributed by the scattering from the red blood cell. When the blood flow moves away from the transmitter, the relationship between the center frequencies is Fb<Fs, or when the blood flow moves toward the transmitter, the relationship is Fb>Fs. The difference between the center frequencies Fs and Fb is referred to as a Doppler shift frequency.

Since the reflected wave is a mixture of the tissue echo and the blood flow echo, the echoes are then separated in the band pass filtering means 3a, 3b. FIG. 2 shows frequency characteristics of the band pass filtering means 3a, 3b. The band pass filtering means 3a only allows a frequency band centering on Fs to be passed, and the band pass filtering means 3b only allows a frequency band centering on Fb to be passed. The tissue echo and the blood flow echo can be extracted separately in this way, and then are synthesized for B-mode display.

Thanks to the development in the digital technology, a filter with good cut-off characteristics serving as the band pass filtering means 3a, 3b can be realized. Thus, the blood vessel wall 6, which is a tissue, and the blood flow 5 inside the blood vessel wall 6 can be displayed simultaneously on the B-mode display screen 4, as shown in FIG. 3.

Here, only the frequency bands of the reflected wave centering on the center frequency Fs of the tissue echo and on the center frequency Fb of the blood flow echo are passed, and the other frequency components to cause noise are cut off. In this way, both the tissue and the blood flow can be displayed vividly.

Now, referring to FIG. 4, an ultrasonic diagnostic apparatus that implements the method of imaging a blood flow will be described.

The transmitting/receiving unit 10 emits an ultrasonic beam of a frequency Fs, and receives the tissue echo and the blood flow echo from a human body (not shown). The tissue echo has the center frequency Fs, and the blood flow echo has the center frequency Fb. The echo including the two echoes is converted into a digital signal in the AD converting unit 11. The section described so far is referred to as a front-end section.

Then, only a specified frequency band passes through the band pass filtering (BPF) unit 12. The band pass filtering (BPF) unit 12 has two band pass filter means 3a and 3b. The band pass filtering 3a allows only the frequency band centering on Fs of the input echo to be passed therethrough, and the band bass filtering means 3b allows only the frequency band centering on Fb to be passed therethrough. Thus, the tissue echo and the blood flow echo are extracted separately.

The tissue echo having passed through the band pass filter means 3a and the blood flow echo having passed through the band pass filter means 3b are superimposed on each other and fed to the detecting unit 13, where detection is carried out. Since the echo can be regarded as one modulated by amplitude modulation, an envelope thereof can be derived through orthogonal detection or the like.

Then, the amplifying unit 14 amplifies the detected signal. Since the ultrasonic echo has a quite wide dynamic range, amplification of which relationship between the input and the output having a logarithmic, rather than linear, is performed so that signal strength falls within a certain range. In addition, a high frequency component is removed by the low-pass filtering (LPF) unit 15. In this case, a frequency band equal to or lower than a half of a sampling frequency in the AD conversion is passed through the low-pass filtering unit. The section from the BPF unit 12 to the LPF unit 15 is referred to as an intermediate processing section.

Then, the image generating unit 16 generates an image that can be displayed on a monitor. If the data received from the intermediate processing section is in polar coordinates, it is converted into orthogonal coordinates. In addition, an interpolation or the like is performed on a region with less pixels. The data generated is temporarily stored in the frame memory (FM) unit 17, and then displayed on the display unit 18 in B-mode as a motion picture.

Now, setting of the center frequency Fb of the band pass filter means 3b will be described. The setting is accomplished manually or automatically. The center frequency Fb used for determining the Doppler shift frequency is not known when measurement is started. Therefore, a relatively wide pass band of the band pass filter means is previously established, the reflection echo of the ultrasonic beam is received for all the frequency band, and then a predetermined frequency bandwidth including the center frequency Fs of the transmitted ultrasonic beam is scanned for a signal component having a level more than predetermined one. This scan is performed while viewing the B-mode display screen. If the signal component is found, the frequency having the waveform is determined as the center frequency Fb. Alternatively, the center frequency Fb is adjusted so that the blood flow is displayed vividly by shifting the frequency while viewing the B-mode display screen. The scan may be performed manually by a user directly viewing the B-mode display screen or automatically with predetermined analyzing means.

When automatically performed, the Doppler shift may be automatically measured to determine the center frequency Fb. That is, a frequency analysis, such as Fourier analysis, can be performed on the input echo to provide a power spectrum thereof including waveform peaks of the ultrasonic beam corresponding to the center frequencies Fs and Fb Based on the power spectrum and the known center frequency Fs, the center frequency Fb can be calculated.

In either case, thanks to the development in the digital technology, the center frequency and pass band of the filter can be relatively readily made variable.

As described above, according to this embodiment, the tissue echo and the blood flow echo are separated in terms of frequency region. Therefore, in the case where these echoes are to be displayed in B-mode in real time, even if the tissue and the blood flow are physically close to each other, they can be distinguished and displayed vividly.

According to a conventional method, such like color echo, of calculating the direction and intensity of a section of the blood flow using the Doppler effect, generating a color image reflecting the velocity of the flow, and superimposing the color image on the B-mode image is required a complicated processing, such as an autocorrelation operation or fast Fourier transform, for generating the color image, and thus, an enormous amount of calculation is required. On the contrary, according to this embodiment, which also involves the Doppler effect, only the B-mode images of the tissue and blood flow are generated, and therefore, the amount of calculation and the cost can be reduced.

In the above-described embodiment, the tissue echo and the blood flow echo are extracted by the two band pass filter means 3a and 3b, respectively, and synthesized in the BPF 12, the synthesized wave is detected in the detecting unit 13, and then the motion pictures of both the tissue and the blood flow are provided in a back end section.

(Embodiment 2)

Figure 6:
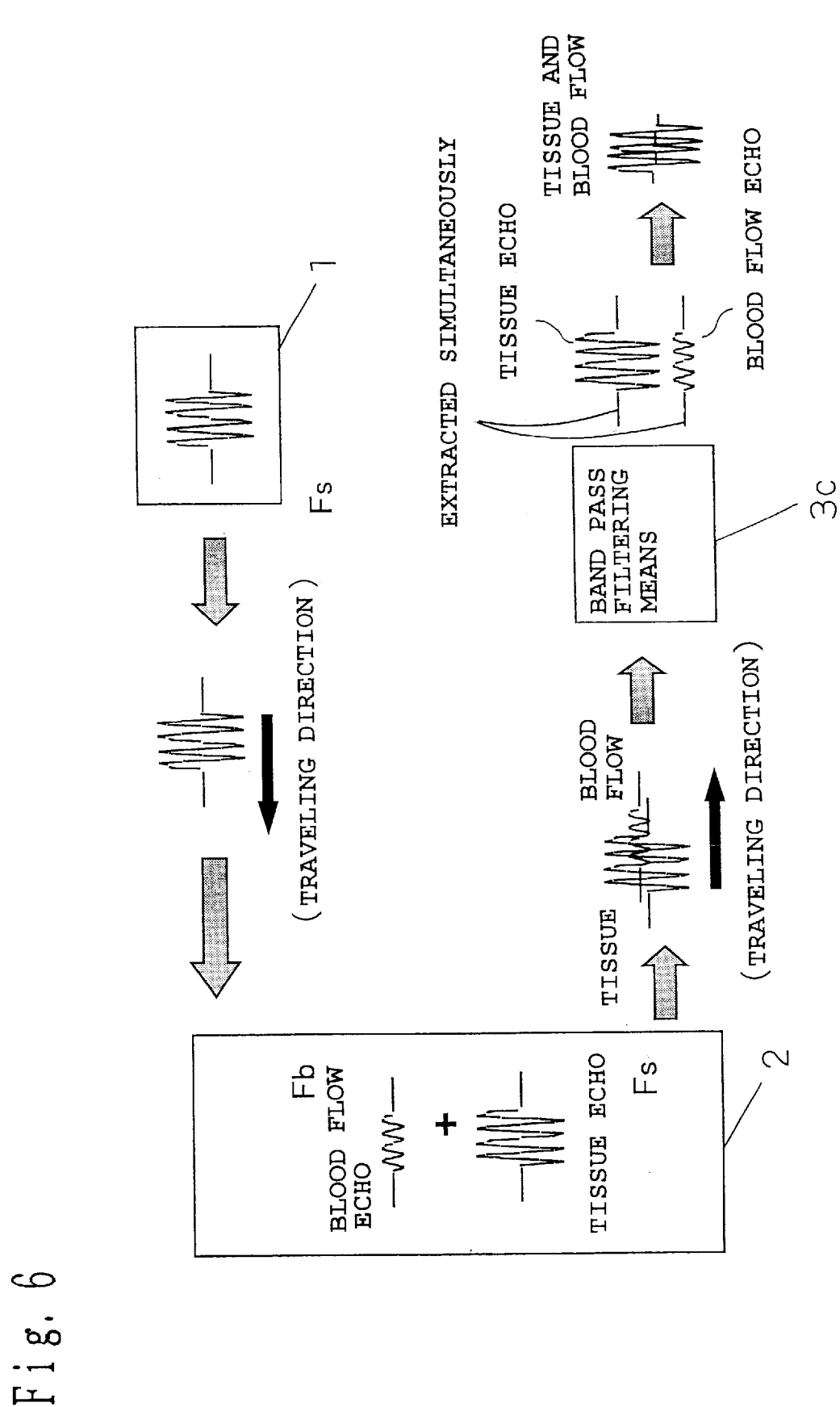
FIG. 6 is a diagram illustrating an operation of a method of imaging a blood flow according to an embodiment 2 of this invention.
Figure 7:
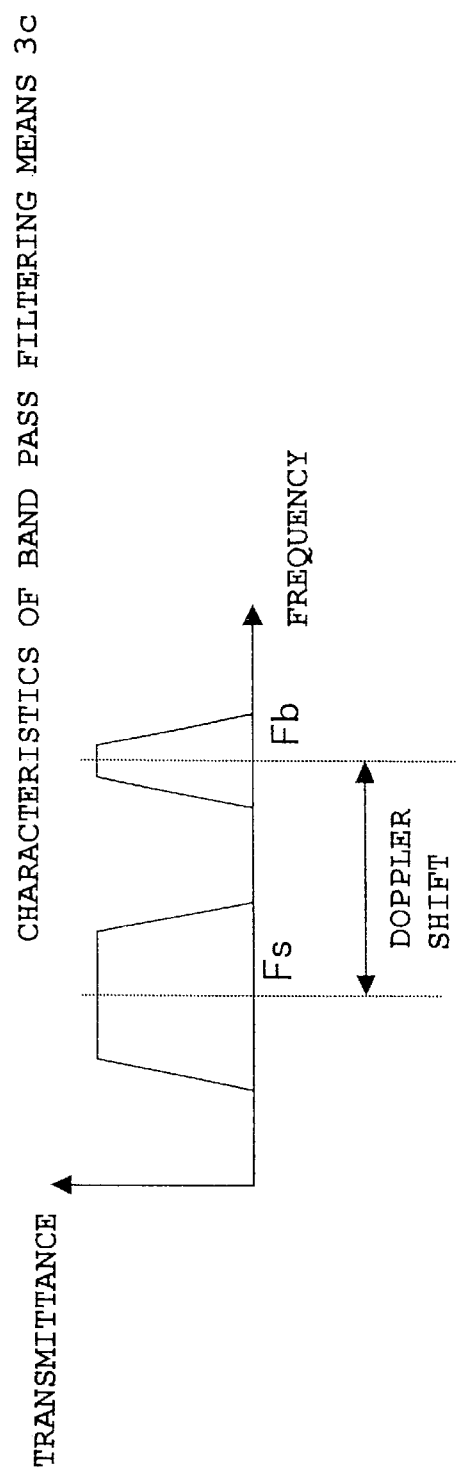
FIG. 7 shows characteristics of band pass filtering means 3c in the embodiment 2 of this invention.

Next, the method of imaging a blood flow according to an embodiment 2 of this invention will be described with reference to the drawings. The description will be made primarily in terms of difference with the embodiment 1. FIG. 6 illustrates an operation of the method of imaging a blood flow according to the embodiment 2 of this invention, and FIG. 7 shows characteristics of the band pass filtering means in this embodiment.

The operation according to this embodiment is as follows. As in the embodiment 1, the transmitting means 1 first emits the ultrasonic beam having the center frequency Fs, and the tissue echo having the center frequency Fs and the blood flow echo having the center frequency Fb return. The tissue echo and the blood flow echo, which are mixed with each other, are separated in the band pass filtering means 3c. As shown in FIG. 7, the band pass filtering means 3c allows only two bands of the input signal centering on the center frequencies Fs and Fb corresponding to first and second pass bands according to this invention, respectively, to pass therethrough. In this way, the tissue echo and the blood flow echo can be extracted separately, and these echoes are synthesized and displayed in B-mode.

The band pass filtering means 3c is a single filter having two bands of first and second pass bands, and the cut off characteristics thereof are inferior to those of the BPF unit 12 including two band pass filter means 3a, 3b each having one pass band according to the embodiment 1. However, since only one band pass filtering means is needed, the implementation of the whole apparatus is advantageously simplified.

Figure 13:
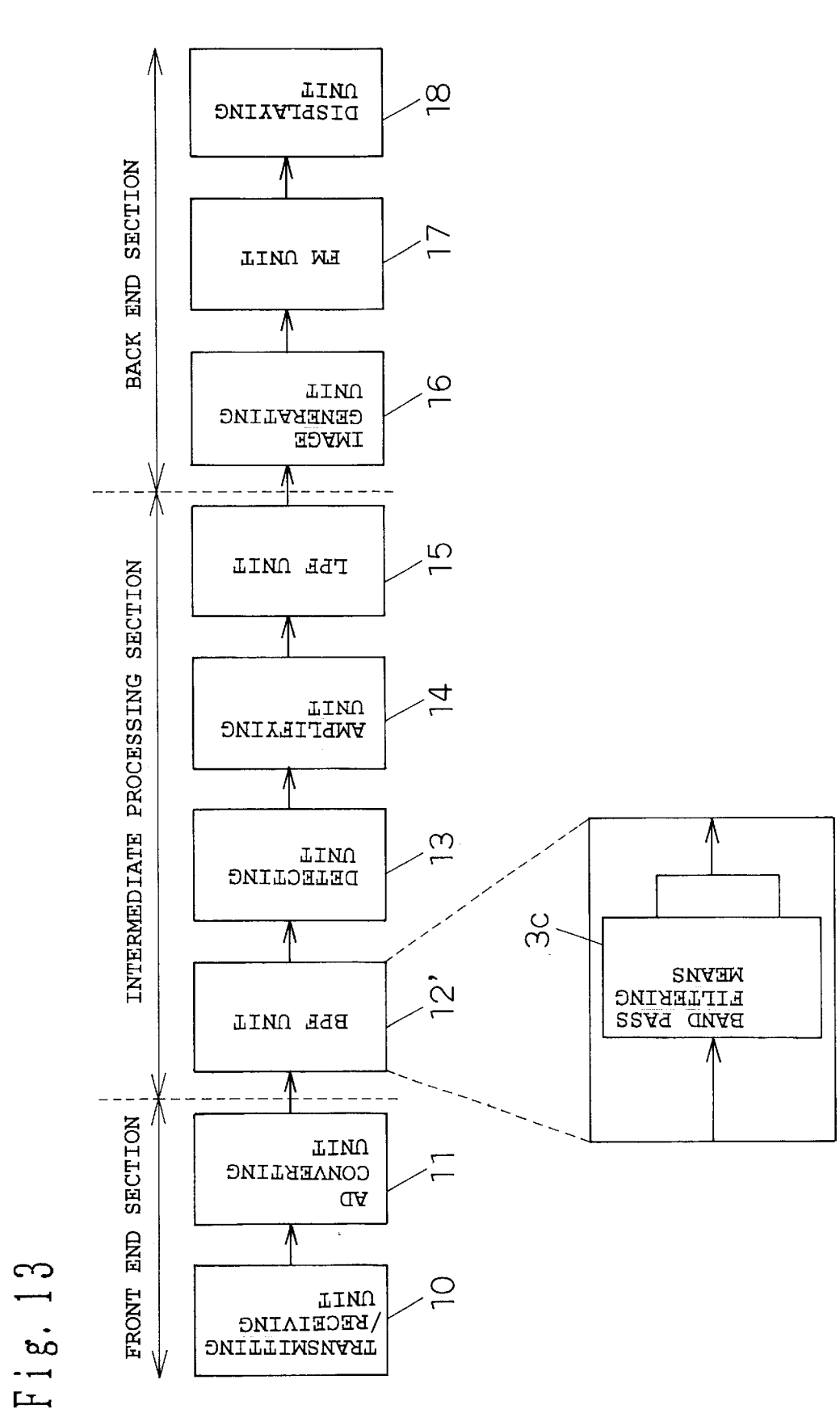
FIG. 13 is a block diagram of the ultrasonic diagnostic apparatus according to the embodiment 2 of this invention.

FIG. 13 is a block diagram of the ultrasonic diagnostic apparatus involving the method of imaging a blood flow according to this embodiment. In FIG. 13, parts similar or corresponding to those in FIG. 4 are assigned the same reference numerals as in FIG. 4, and detailed descriptions thereof are omitted. A BPF unit 12' is different from the BPF unit 12 in that it has a single band pass filter means 3c. The operation of the ultrasonic diagnostic apparatus is the same as in the embodiment 1 except that the BPF unit 12' having the band pass filtering means 3c operates as described above.

(Embodiment 3)

Figure 8:
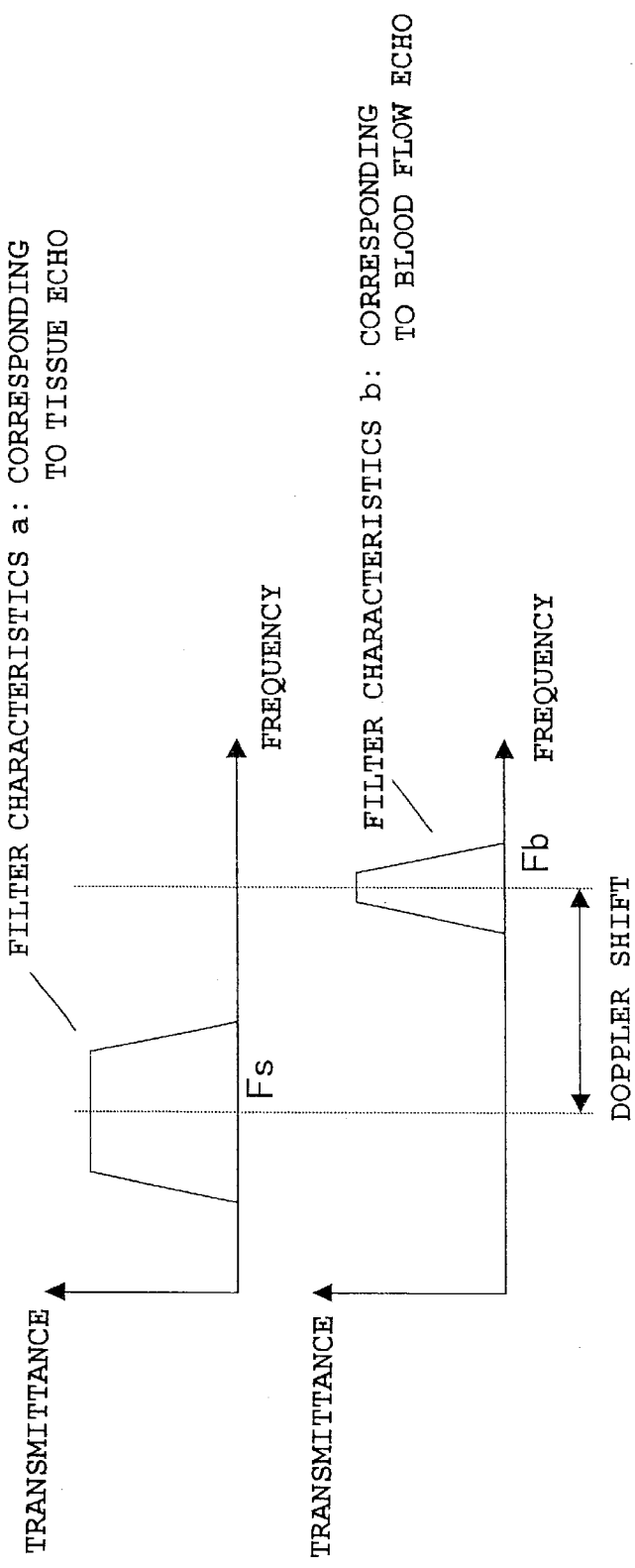
FIG. 8 shows characteristics of band pass filtering means 3d in the embodiment 3 of this invention.
Figure 10:
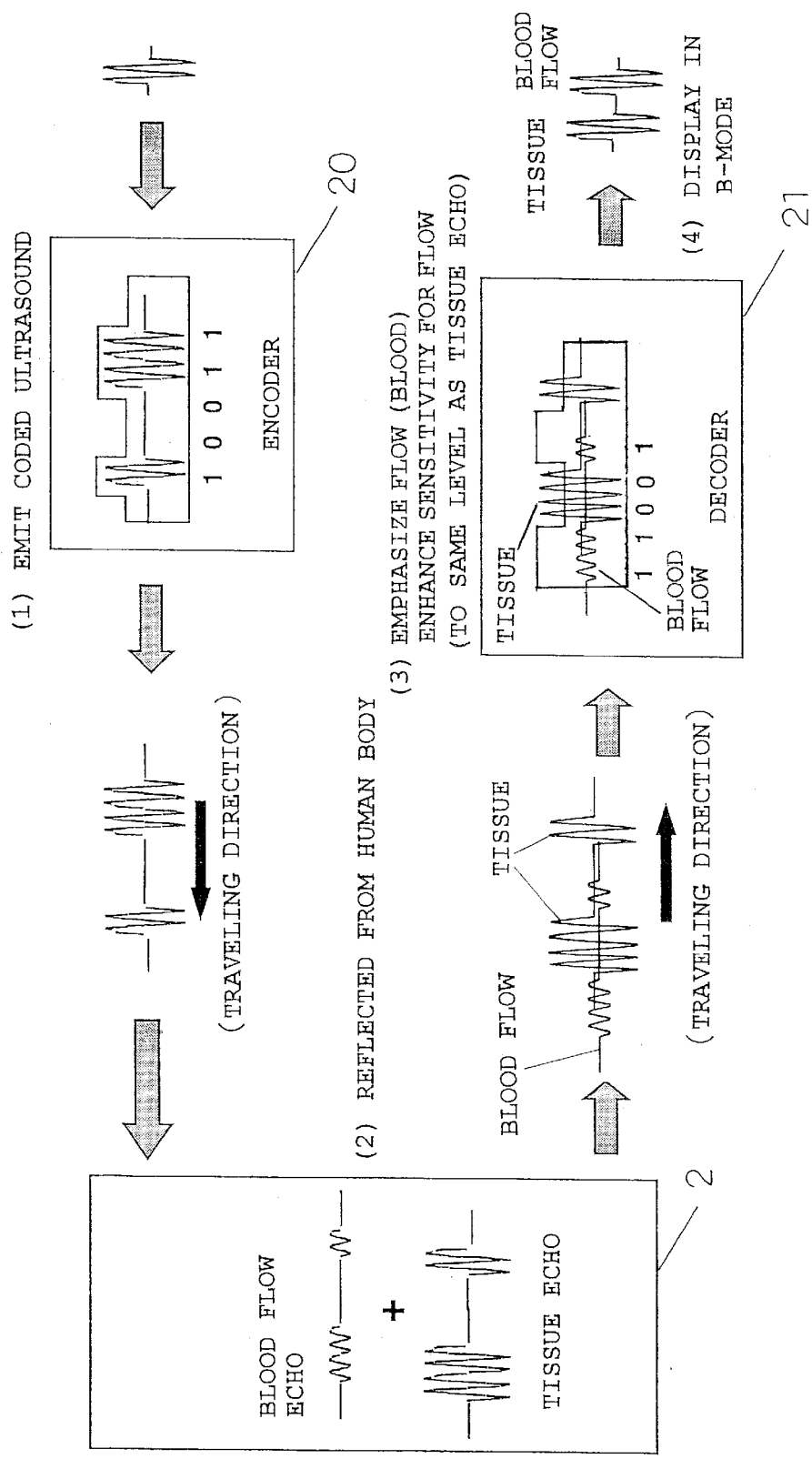
FIG. 10 is a diagram illustrating an operation of a method of displaying a blood flow in a conventional ultrasonic diagnostic apparatus.

Next, the method of imaging a blood flow according to an embodiment 3 of this invention will be described with reference to the drawings. The description will be made primarily in terms of difference with the embodiments 1 and 2. FIG. 8 shows characteristics of the band pass filtering means in this embodiment, and FIGS. 9(A), 9(B) and 9(C) are timing charts according to this embodiment. In addition, FIG. 14 illustrates an operation of the method of imaging a blood flow according to the embodiment 3 of this invention.

Figure 14:
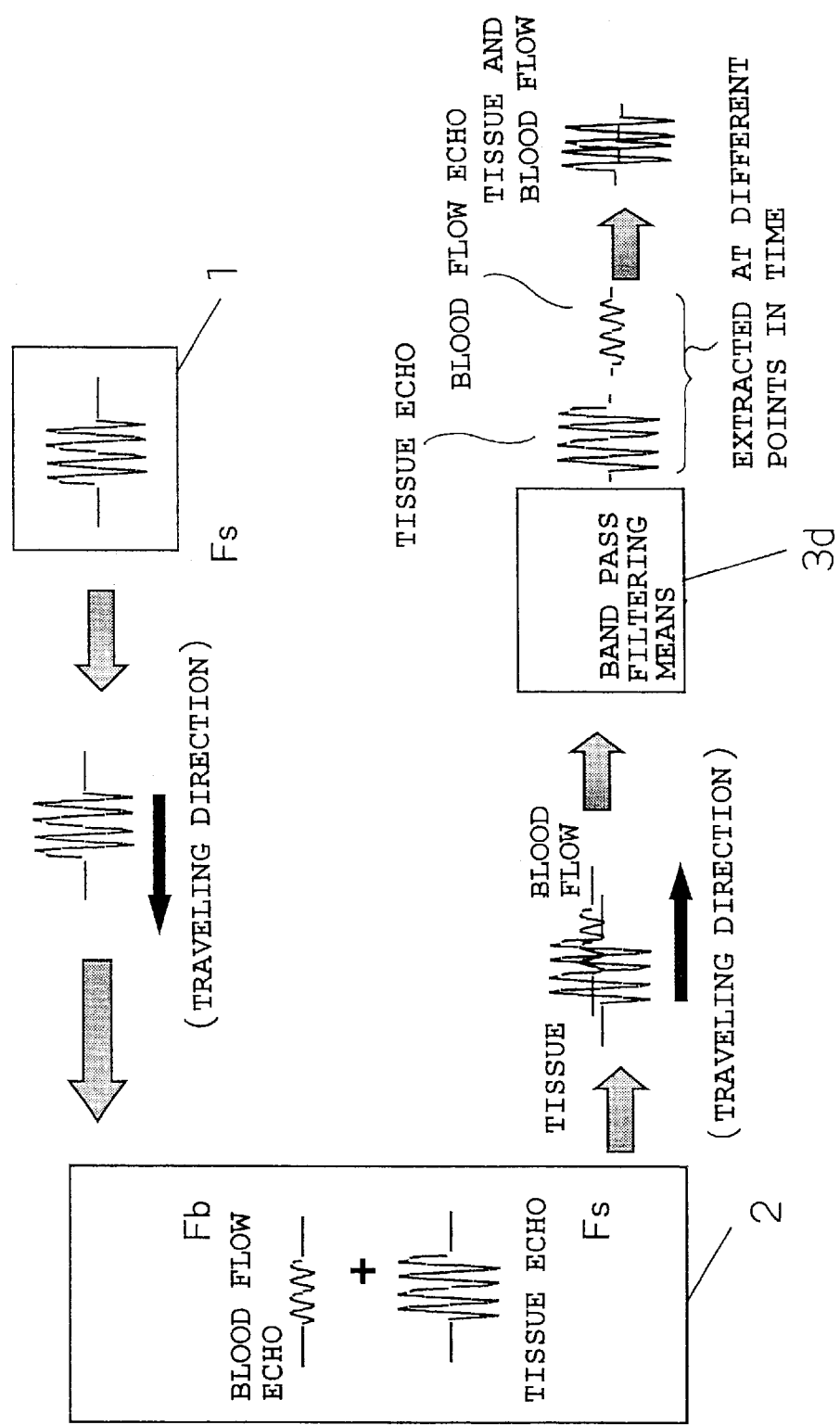
FIG. 14 is a diagram illustrating an operation of a method of imaging a blood flow according to an embodiment 3 of this invention.

With reference to FIG. 14, the operation of the method of imaging a blood flow will be described. As in the embodiment 2, when the transmitting means 1 emits the ultrasonic beam having the center frequency Fs to the human body 2, the tissue echo having the center frequency Fs and the blood flow echo having the center frequency Fb return. Since the tissue echo and the blood flow echo are mixed with each other, these echoes are separated, in terms of time, in band pass filtering means 3d, which is a single filter having two pass bands. In other words, the echoes are extracted with a time lag, rather than simultaneously.

As shown in FIG. 8, the band pass filtering means 3d has two types of filter characteristics a and b, which are switched from one to another in terms of time so that only one of two filter characteristics is used in one operation. The filter characteristics a and b are to pass bands centering on the center frequencies Fs and Fb through the filter, respectively, and are used to pass the tissue echo and the blood flow echo through the filter, respectively.

The filter characteristics are switched as shown in FIGS. 9(A), 9(B) and 9(C). As shown in FIG. 9(A), the transmitting means 1 emits the ultrasonic signal (short wave) at regular time intervals. Then, echoes return from the human body 2 at regular intervals. The echo is a mixture wave of the tissue echo and the blood flow echo, as shown in FIG. 9(B).

The mixture wave is allowed to pass through the filtering means by switching between the filter characteristics a and the filter characteristics b in the ratio 1 to 3, specifically, by adopting the filter characteristics a, b, b, and b, in this order. Since the tissue echo is selectively allowed to pass the filter when the characteristics a is used, and the blood flow echo is selectively allowed to pass the filter when the characteristics b is used, according to the switching order described above, the tissue echo, the blood flow echo, the blood flow echo and the blood flow echo are extracted from the input mixture wave in this order. Thus, a waveform having passed through the filter as shown in FIG. 9(C) is obtained.

Eventually, the tissue echo and the blood flow echo can be extracted in a time-divisional manner, and these echoes are synthesized and displayed in B-mode.

According to this embodiment, the cut off characteristics of the band pass filter can be similar to that in the embodiment 1, and further advantageously, the cut off characteristics can be attained with the single band pass filter means 3d. In the case of generating the motion picture, since the tissue echo is received intermittently, the frame rate for a part associated therewith is reduced. However, the reduction does not have so much adverse influence on the generated picture because the tissue is stationary object.

Figure 15:
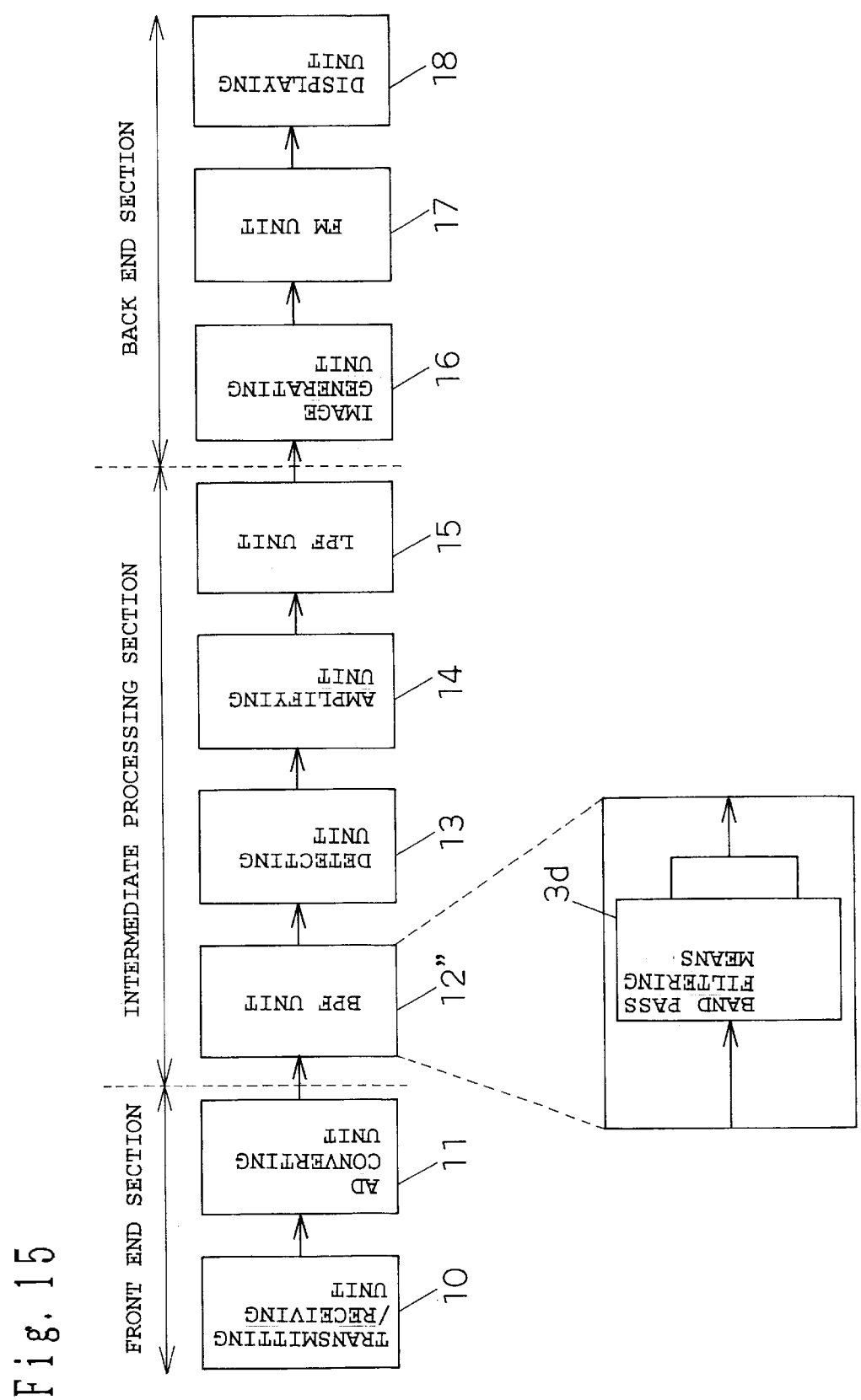
FIG. 15 is a block diagram of the ultrasonic diagnostic apparatus according to the embodiment 3 of this invention.
Figure 16:
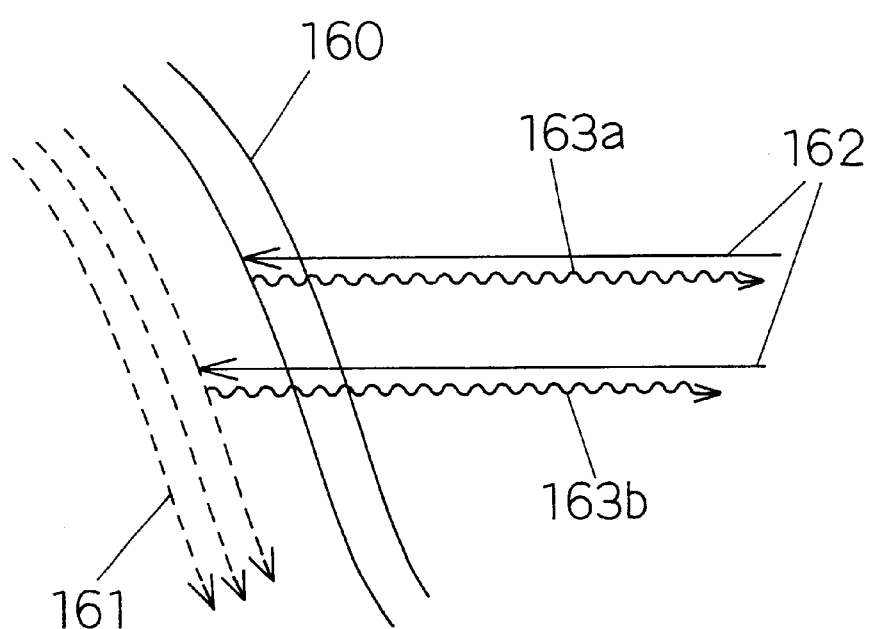
FIG. 16 illustrates a method of displaying a blood flow in a conventional ultrasonic diagnostic apparatus.

FIG. 15 is a block diagram of the ultrasonic diagnostic apparatus involving the method of imaging a blood flow according to this embodiment. In FIG. 15, parts similar or corresponding to those in FIG. 4 are assigned the same reference numerals as in FIG. 4, and detailed descriptions thereof are omitted. A BPF unit 12" has the above-described band pass filtering means 3d. The operation of the ultrasonic diagnostic apparatus is the same as in the embodiment 1 except that the BPF unit 12" having the band pass filtering means 3d operates as described above.

While the selection ratio of the filter characteristics a to the filter characteristics b is 1 to 3 in the above description, the selection ratio is not limited to the values and may be 1 to 1. For displaying the motion picture, however, it is desired that the number of times of selection of the filter characteristics b is higher than that of the filter characteristics a.

(Embodiment 4)

The ultrasonic diagnostic apparatus according to an embodiment 4 of this invention has the front end section similar to that in the embodiment 1 and the intermediate processing section and back end section duplexed so that the image for the blood flow echo and the image for the tissue echo can be generated separately.

Figure 11:
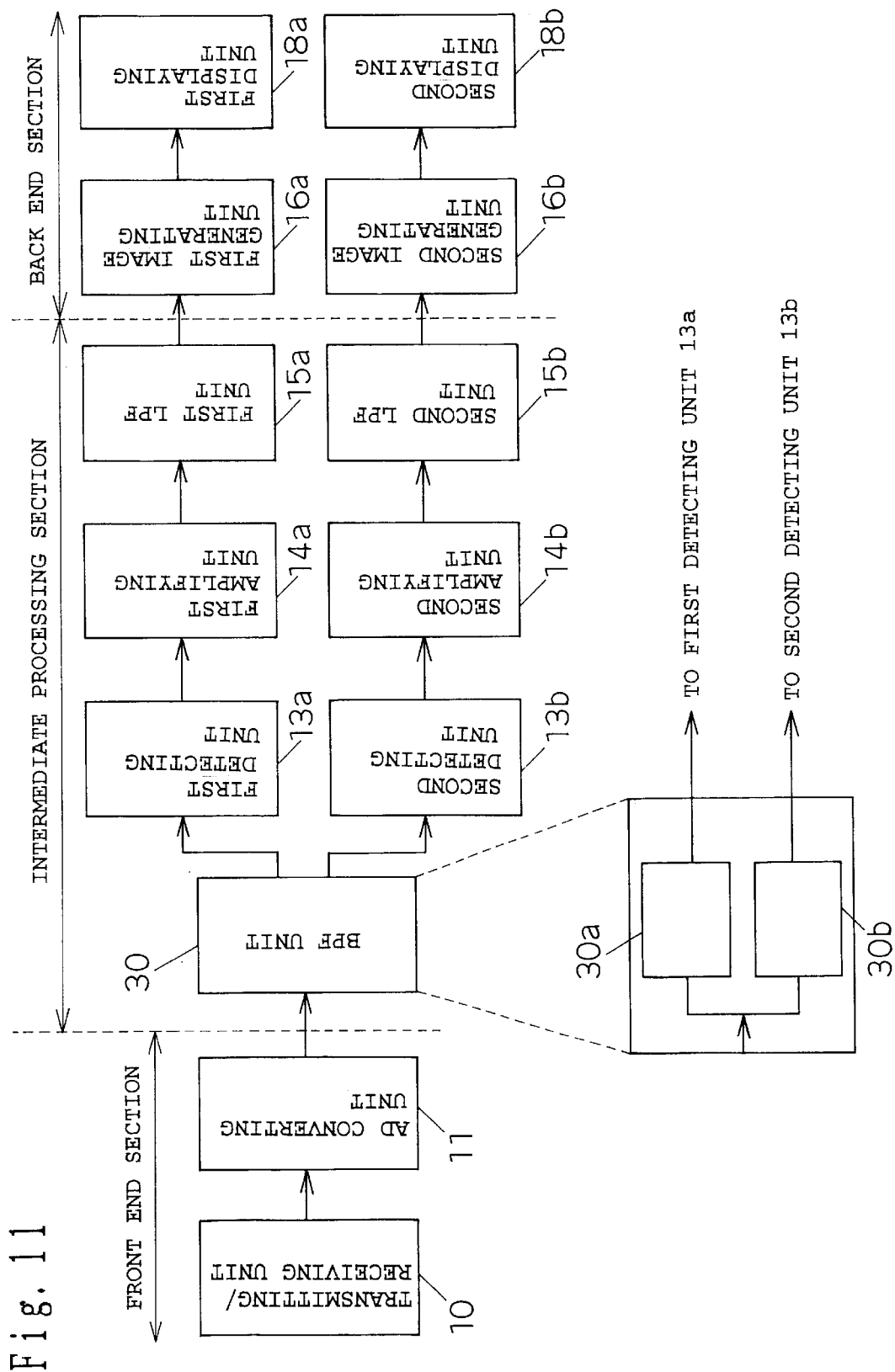
FIG. 11 is a block diagram of the ultrasonic diagnostic apparatus according to the embodiment 4 of this invention.

FIG. 11 is a block diagram of the ultrasonic diagnostic apparatus implementing the method of imaging a blood flow according to this embodiment. In FIG. 11, parts similar or corresponding to those in FIG. 4 are assigned the same reference numerals as in FIG. 4, and detailed descriptions thereof are omitted. Reference numeral 30 denotes a BPF unit that extracts the blood flow echo and the tissue echo from the received wave, reference numeral 13a denotes a first detecting unit that detects the tissue echo, reference numeral 14a denotes a first amplifying unit that amplifies a detected signal, reference numeral 15a denotes a low-pass filtering (LPF) unit that removes a high frequency component, reference numeral 13b denotes a second detecting unit that detects the blood flow echo, reference numeral 14b denotes a second amplifying unit that amplifies a detected signal, and reference numeral 15b denotes a low-pass filter (LPF) unit that removes a high frequency component.

The BPF unit 30 includes two band pass filtering means 30a and 30b. The band pass filtering means 30a allows the frequency band of the input echo centering on the frequency Fs to pass therethrough to extract the tissue echo separately, and the band pass filtering means 30b allows the frequency band of the input echo centering on the frequency Fb to pass therethrough to extract the blood flow echo separately. This embodiment differs from the embodiment 1 in that the tissue echo extracted by the band pass filtering means 30a is output to the first detecting unit 13a as it is, and the blood flow echo extracted by the band pass filtering means 30b is output to the second detecting unit 13b as it is. These constitute the intermediate processing section of this embodiment.

Reference numeral 16a denotes a first image generating unit that generates an image from a signal output from the first LPF unit 15a, and reference numeral 18a denotes a first displaying unit that displays the image generated by the first image generating unit 16a. Reference numeral 16b denotes a second image generating unit that generates an image from a signal output from the second LPF unit 15b, and reference numeral 18b denotes a second displaying unit that displays the image generated by the second image generating unit 16b. These constitute the back end section of this embodiment.

Figure 5:
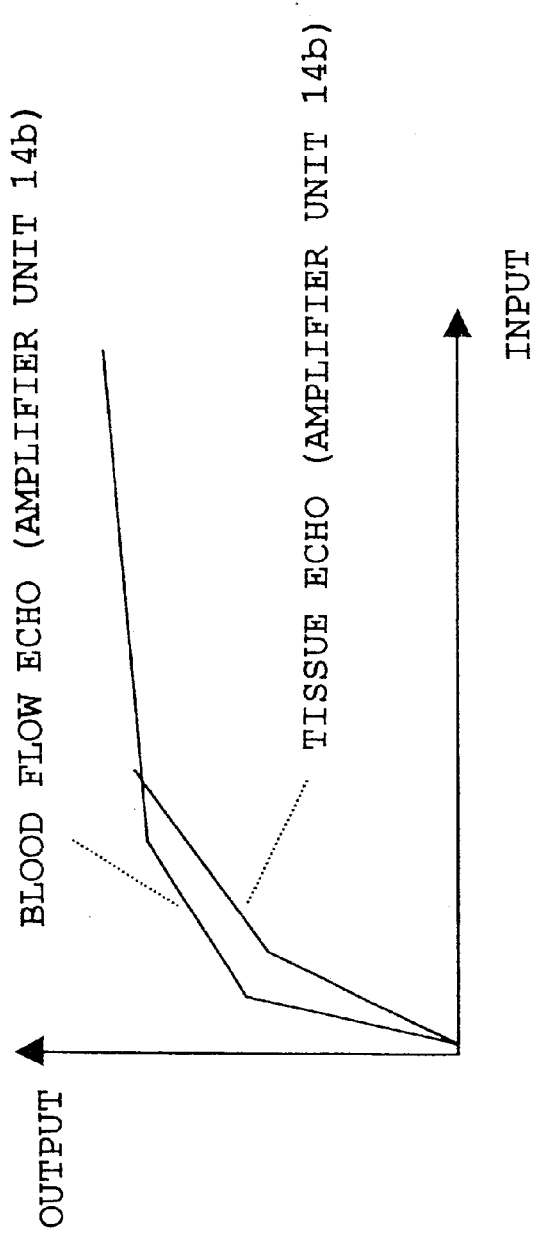
FIG. 5 shows characteristics of an amplifier units 14a, 14b according to an embodiment 4 of this invention.

FIG. 5 shows characteristics of the amplifying units 14a, 14b of this ultrasonic diagnostic apparatus.

The ultrasonic diagnostic apparatus having such a arrangement according to this embodiment operates in the following manner. The transmitting/receiving unit 10 and the AD converting unit 11 operate as in the embodiment 1.

Then, in the band pass filtering (BPF) unit 30, the band pass filtering means 30a allows the frequency band of the input echo centering on the frequency Fs to pass therethrough and outputs the frequency band to the first detecting unit 13a as the tissue echo. The band pass filtering means 30b allows the frequency band of the input echo centering on the frequency Fb and outputs the frequency band to the second detecting unit 13b as the blood flow echo.

Now, the following description will be mainly focused on the tissue echo. The tissue echo extracted by the band pass filtering means 30a is fed to first the detecting unit 13a, where detection is carried out. Since the echo can be regarded as amplitude modulated, an envelope thereof can be derived through orthogonal detection or the like.

Then, the first amplifying unit 14a amplifies the detected signal. Since the ultrasonic echo has a quite wide dynamic range, amplification having a logarithmic, rather than linear, relationship between the input and the output is adopted so that signal strength falls within a certain range. In addition, a high frequency component is removed by the low-pass filter (LPF) unit 15a. In this case, a frequency band equal to or lower than a half of a sampling frequency in the AD conversion is passed through the low-pass filtering unit.

Then, the first image generating unit 16a generates an image that can be displayed on a monitor. If the data received from the intermediate processing section is in polar coordinates, it is converted into orthogonal coordinates. In addition, an interpolation or the like is performed on a region with less pixels. Finally, the generated image is displayed on the first displaying unit 18a.

The operation described so far results in an ultrasonic tomogram for only the tissue of the human body.

As for the blood flow echo, the second detecting unit 13b operates the same as the first detecting unit 13a, the second amplifying unit 14b operates the same as the first amplifying unit 14a, the second LPF unit 15b operates the same as the first LPF unit 15a, the second image generating unit 16b operates the same as the first image generating unit 16a, and the second display unit 18b operates the same as the first displaying unit 18a. Thus, an ultrasonic tomogram for the blood flow in the human body can be provided. Here, while the amplifying units 14a and 14b may have the same characteristics, they desirably have the characteristics as shown in FIG. 5. That is, in a region for a low input, an amplification factor for the blood flow echo is kept higher than that for the tissue echo. The blood flow echo is weaker than the tissue echo, and keeping the amplification factor for the blood flow echo higher can provide an image with the blood echo being emphasized.

The operation described so far can provide the ultrasonic tomograms for the tissue and blood flow separately, and therefore, the blood flow and the tissue can be easily distinguished.

Figure 12:
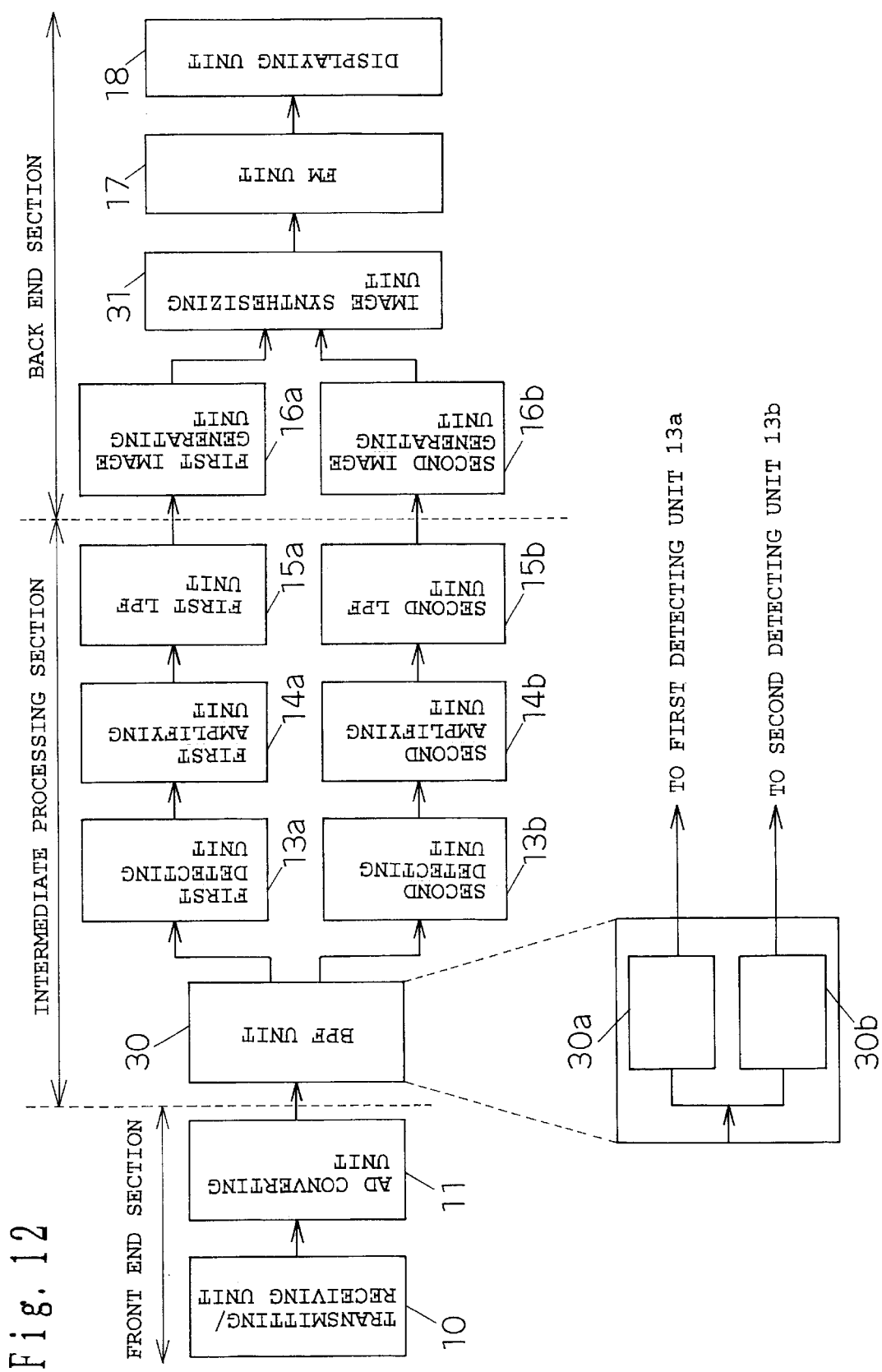
FIG. 12 is a block diagram showing another arrangement of the ultrasonic diagnostic apparatus according to the embodiment 4 of this invention.

This embodiment may be implemented with an arrangement shown in FIG. 12. With the exemplary arrangement shown in FIG. 12, the ultrasonic tomogram for the tissue of the human body generated in the first image generating unit 16a and the ultrasonic tomogram for the blood flow in the human body generated in the second image generating unit 16b are synthesized in an image synthesizing unit 31, thereby providing one synthesized image. The synthesized image is temporarily stored in the frame memory (FM) unit 17, and then displayed on the displaying unit 18 in B-mode as a motion picture, as in the embodiment 1.

This arrangement is the same as that of the embodiment 1 in that the tissue and the blood flow can be simultaneously displayed in real time, but differs therefrom in that the images of the tissue and blood flow are generated separately in the first image generating unit 16a and the second image generating unit 16b, respectively. Thus, there is an advantage in that an image processing, such as contour enhancement and brightness enhancement, can be performed on each image to provide the synthesized motion picture with more explicit boundary between the tissue and the blood flow in the human body. Here, only the image of the tissue generated in the first image generating unit 16a may be processed, and the image of the blood flow generated in the second image generating unit 16b is not processed, and vice verse. Alternatively, both the images generated in the first and second image generating units 16a and 16b may be processed.

While the arrangement shown in FIG. 12 includes the frame memory 17 and provides the motion picture in the above description, the frame memory 17 may be omitted and the synthesized image may be provided in the form of still image.

In the description of this embodiment, in either arrangement shown in FIG. 11 or FIG. 12, the BPF unit 30 includes two band pass filtering means 30a and 30b as in the embodiment 1. However, the BPF unit 30 may be implemented in the form of the band pass filtering means 3c in the embodiment 2 or the band pass filtering means 3d in the embodiment 3.

In the above-described embodiments, the transmitting/receiving unit 1 is equivalent to ultrasonic transmitting means and ultrasonic receiving means of this invention. The BPF unit 12, 12', 12'', 30 are equivalent to filtering means of this invention. The intermediate processing section, the image generating unit 16, the first image generating unit 16a and the second image generating unit 16b are equivalent to image generating means of this invention. The image synthesizing unit 31 is equivalent to image processing means and image synthesizing means of this invention. The band pass filtering means 3a is equivalent to a first sub-filter of this invention, and the band pass filtering means 3b is equivalent to a second sub-filter of this invention. The band pass filtering means 3c and 3d are equivalent to filtering means of this invention. The band for passing the tissue echo is equivalent to a first frequency band of this invention, and the band for passing the blood flow echo is equivalent to a second frequency band of this invention.

In addition, the human body 2, the tissue and the blood flow in the human body are equivalent to an object body of this invention. The blood flow is equivalent to an object body serving to provide a Doppler shift of this invention.

In the above description of the embodiments, there are provided two band pass filtering means including the band pass filter means 3a equivalent to the first sub-filter of this invention and the band pass filtering means 3b equivalent to the second sub-filter of this invention. According to this invention, however, two or more second sub-filters as the second sub-filters of this invention may be provided, and the plurality of second sub-filters may allows the echo to pass therethrough in second frequency bands higher than the first frequency band and lower than the first frequency band. In this case, the blood flow moving away from a tissue in the human body and the blood flow moving toward the tissue in the human body can be displayed simultaneously, and thus, a turbulent flow or back flow in the object body can be observed. Here, the plurality of second frequency bands may comprise only frequency bands higher than the first frequency band or only frequency bands lower than the first frequency band.

Besides, the band pass filter means 3c may have a plurality of second frequency bands as in the case of the second sub-filter, and the band pass filter means 3d may have filter characteristics adapted for a plurality of second frequency bands as in the case of the second sub-filter.

The object body serving to provide a Doppler shift of this invention is not limited to the blood flow, or may be a flow of a body fluid in the human body, such as lymph. In addition, the object body is not limited to the human body, or may be a machine with piping and a fluid passing through the pipe. Therefore, this invention is not limited to displaying the blood flow in the human body or ultrasonic diagnosis, or may be applied to product inspection or the like.

As described above, according to this invention, in a B-mode ultrasonic tomogram, a static part and dynamic part of the object body can be displayed vividly and simultaneously as a motion picture.

In addition, according to this invention, in the B-mode ultrasonic tomogram, the static part and dynamic part of the object body can be displayed in such a manner that they can be easily distinguished.

What is claimed is:

1. An ultrasonic tomography apparatus, comprising:

ultrasonic transmitting means of transmitting an ultrasound to an object body;

ultrasonic receiving means of receiving the ultrasound reflected from said object body and producing an ultrasonic signal;

filtering means of extracting components of said ultrasonic signal in at least two different frequency bands; and image generating means of generating an ultrasonic tomogram of said object body based on said extracted ultrasonic signal component in a first frequency band and said extracted ultrasonic signal component in one or more second frequency bands, wherein said first frequency band centers on a frequency band at the time of said transmission, said second frequency band is shifted from the frequency band at the time of said transmission, and said second frequency band is set centered on a frequency for which a signal component is detected by scanning a predetermined bandwidth allowing for a potential Doppler shift from said first frequency band.

2. An ultrasonic tomography apparatus, comprising:

ultrasonic transmitting means of transmitting an ultrasound to an object body;

ultrasonic receiving means of receiving the ultrasound reflected from said object body and producing an ultrasonic signal;

filtering means of extracting components of said ultrasonic signal in at least two different frequency bands; and image generating means of generating a first partial ultrasonic tomogram of said object body based on said extracted ultrasonic signal component in a first frequency band and a second partial ultrasonic tomogram of said object body based on said ultrasonic signal component in one or more second frequency bands, wherein said first frequency band centers on a frequency band at the time of said transmission, said second frequency band is shifted from the frequency band at the time of said transmission, and said second frequency band is set centered on a frequency for which a signal component is detected by scanning a predetermined bandwidth allowing for a potential Doppler shift from said first frequency band.

3. The ultrasonic tomography apparatus according to claim 2, further comprising:

image processing means of performing an image processing on at least one of said first partial ultrasonic tomogram and said second partial ultrasonic tomogram; and image synthesizing means of producing an ultrasonic tomogram by performing any of (1) synthesis of the first partial ultrasonic tomogram subject to said image processing and the second partial ultrasonic tomogram not subject to said image processing, (2) synthesis of the first partial ultrasonic tomogram not subject to said image processing and the second partial ultrasonic tomogram subject to said image processing, and (3) synthesis of the first partial ultrasonic tomogram subject to said image processing and the second partial ultrasonic tomogram subject to said image processing.

4. The ultrasonic tomography apparatus according to claim 1 or 2, wherein said second frequency band is set centering on a frequency for which a signal component having a level more than predetermined one is detected by frequency-analyzing said received reflected ultrasonic.

5. The ultrasonic tomography apparatus according to claim 4, wherein said filtering means includes:
   a first sub-filter for allowing said first frequency band to pass therethrough; and
   one or more second sub-filters for allowing said second frequency band to pass therethrough.

6. The ultrasonic tomography apparatus according to claim 4, wherein said filtering means is set a first pass band for allowing said first frequency band to pass through the filtering means and a second pass band for allowing said second frequency band to pass through the filtering means, and
   said first pass band and said second pass band allow signals to pass therethrough simultaneously.

7. The ultrasonic tomography apparatus according to claim 4, wherein said filtering means allows said first frequency band or said second frequency band to pass therethrough selectively, and
   said image generating means performs an operation using the ultrasonic signal component in said first frequency band and an operation using the ultrasonic signal component in said second frequency band in a time-divisional manner.

8. The ultrasonic tomography apparatus according to claim 7, wherein in said filtering means, the number of times of selection of said second frequency band is higher than that of said first frequency band.

9. The ultrasonic tomography apparatus according to claim 4, wherein said image generating means includes amplifying moans of amplifying a signal having passed through said first frequency band and/or a signal having passed through said second frequency band, and
   said amplifying means amplifies the signal having passed through said second frequency band more than the signal having passed through said first frequency band.

10. The ultrasonic tomography apparatus according to claim 4, wherein said object body is a human body,
    said first frequency band is a frequency band of an echo from a tissue of said human body, and
    said second frequency band is a frequency band of an echo from a blood flow in said human body.

11. The ultrasonic tomography apparatus according to claim 1 or 2, wherein said filtering means includes:
    a first sub-filter for allowing said first frequency band to pass therethrough; and
    one or more second sub-filters for allowing said second frequency band to pass therethrough.

12. The ultrasonic tomography apparatus according to claim 1 or 2, wherein said filtering means is set a first pass band for allowing said first frequency band to pass through the filtering means and a second pass band for allowing said second frequency band to pass through the filtering means, and
    said first pass band and said second pass band allow signals to pass therethrough simultaneously.

13. The ultrasonic tomography apparatus according to claim 1 or 2, wherein said filtering means allows said first frequency band or said second frequency band to pass therethrough selectively, and
    said image generating means performs an operation using the ultrasonic signal component in said first frequency band and an operation using the ultrasonic signal component in said second frequency band in a time-divisional manner.

14. The ultrasonic tomography apparatus according to claim 13, wherein in said filtering means, the number of times of selection of said second frequency band is higher than that of said first frequency band.

15. The ultrasonic tomography apparatus according to claim 1 or 2, wherein said image generating means includes amplifying means of amplifying a signal having passed through said first frequency band and/or a signal having passed through said second frequency band, and
    said amplifying means amplifies the signal having passed through said second frequency band more than the signal having passed through said first frequency band.

16. The ultrasonic tomography apparatus according to claim 1 or 2, wherein said object body is a human body,
    said first frequency band is a frequency band of an echo from a tissue of said human body, and
    said second frequency band is a frequency band of an echo from a blood flow in said human body.

17. An ultrasonic tomography method, comprising the steps of:
    transmitting an ultrasound to an object body;
    receiving the ultrasound reflected from said object body;
    extracting components of said ultrasound in at least two different frequency bands; and
    generating an ultrasonic tomogram of said object body based on said extracted ultrasonic component in a first frequency band and said extracted ultrasonic component in one or mare second frequency bands,
    wherein said first frequency band centers on a frequency band at the time of said transmission,
    said second frequency band is shifted from the frequency band at the time of said transmission, and
    said second frequency band is set centered on frequency for which a signal component is detected by scanning a predetermined bandwidth allowing for a potential Doppler shift from said first frequency band.

18. An ultrasonic tomography method, comprising the steps of:
    transmitting an ultrasound to an object body;
    receiving the ultrasound reflected from said object body;
    extracting components of said ultrasonic in at least two different frequency bands;
    generating a first partial ultrasonic tomogram of said object body based on said extracted ultrasonic signal component in a first frequency band;
    generating a second partial ultrasonic tomogram of said object body based on said extracted ultrasonic signal component in one or more second frequency bands,
    wherein said first frequency band centers on a frequency band at the time of said transmission,
    said second frequency band is shifted from the frequency band at the time of said transmission, and
    said second frequency band is set centered on a frequency for which a signal component is detected by scanning a predetermined bandwidth allowing for a potential Doppler shift from said first frequency band.

19. The ultrasonic tomography method according to claim 17 or 18, wherein said second frequency band is set centering on a frequency for which a signal component having a level more than predetermined level is detected by frequency-analyzing said received reflected ultrasonic.

* * * * *

UNITED STATES PATENT AND TRADEMARK OFFICE
CERTIFICATE OF CORRECTION

PATENT NO. : 6,685,636 B2  
DATED : February 3, 2004  
INVENTOR(S) : Ichiro Okabayashi et al.

It is certified that error appears in the above-identified patent and that said Letters Patent is hereby corrected as shown below:

Column 15,  
Line 33, "moans" should read -- means --.

Signed and Sealed this

Thirty-first Day of August, 2004

JON W. DUDAS  
*Director of the United States Patent and Trademark Office*